(12) United States Patent
Bui et al.

(10) Patent No.: US 7,617,732 B2
(45) Date of Patent: *Nov. 17, 2009

(54) INTEGRATED CURVED LINEAR ULTRASONIC TRANSDUCER INSPECTION APPARATUS, SYSTEMS, AND METHODS

(75) Inventors: Hien T. Bui, Kent, WA (US); Dennis P. Sarr, Kent, WA (US)

(73) Assignee: The Boeing Company, Chicago, IL (US)

( * ) Notice: Subject to any disclaimer, the term of this patent is extended or adjusted under 35 U.S.C. 154(b) by 398 days.

This patent is subject to a terminal disclaimer.

(21) Appl. No.: 11/368,557

(22) Filed: Mar. 6, 2006

(65) Prior Publication Data

US 2007/0044564 A1 Mar. 1, 2007

Related U.S. Application Data

(63) Continuation-in-part of application No. 11/213,652, filed on Aug. 26, 2005, now Pat. No. 7,444,876.

(51) Int. Cl.
*G01N 29/04* (2006.01)

(52) U.S. Cl. .............................. 73/618; 73/620; 73/635; 73/641

(58) Field of Classification Search .................... 73/618, 73/620, 633, 635, 640, 641, 644, 866.5
See application file for complete search history.

(56) References Cited

U.S. PATENT DOCUMENTS

| | | | |
|---|---|---|---|
| 3,575,042 A | 4/1971 | Lovelace et al. | |
| 3,789,350 A | 1/1974 | Rolle | |
| 3,810,384 A | 5/1974 | Evans | |
| 3,958,451 A | 5/1976 | Richardson | |
| 4,010,636 A | 3/1977 | Clark et al. | |
| 4,064,741 A * | 12/1977 | Reynolds | 73/620 |
| 4,103,234 A | 7/1978 | Frazier, Jr. | |
| 4,112,850 A | 9/1978 | Sigel-Gfeller | |
| 4,117,733 A | 10/1978 | Gugel | |
| 4,160,386 A | 7/1979 | Jackson et al. | |
| 4,167,880 A | 9/1979 | George | |

(Continued)

FOREIGN PATENT DOCUMENTS

DE 28 31 395 A1 1/1980

(Continued)

OTHER PUBLICATIONS

U.S. Appl. No. 10/943,088, filed Sep. 16, 2004; Inventors: Georgeson, entitled *Magnetically Attracted Inspecting Apparatus and Method Using a Ball Bearing*.

(Continued)

*Primary Examiner*—J M Saint Surin
(74) *Attorney, Agent, or Firm*—Alston & Bird LLP

(57) ABSTRACT

Apparatus, systems, and methods for inspecting a structure are provided which use a sensor holder, which is configured to support one or more curved linear inspection sensors and may be constructed from rapid prototyping, such as stereolithography. Integrated curved linear ultrasonic transducer inspection apparatus, systems, and methods provide fast and efficient methods of constructing custom inspection devices and inspecting otherwise difficult-to-inspect curved radius features of structures, such as a corner of a hat stringer.

26 Claims, 3 Drawing Sheets

U.S. PATENT DOCUMENTS

| | | | |
|---|---|---|---|
| 4,173,897 A | 11/1979 | Fostermann et al. | |
| 4,173,898 A | 11/1979 | Fostermann et al. | |
| 4,229,796 A | 10/1980 | Garrett | |
| 4,311,052 A | 1/1982 | Jeffras et al. | |
| 4,327,588 A | 5/1982 | North | |
| 4,365,514 A | 12/1982 | Ho | |
| 4,368,644 A | 1/1983 | Wentzell et al. | |
| 4,399,703 A | 8/1983 | Matzuk | |
| 4,466,286 A | 8/1984 | Berbeé et al. | |
| 4,470,304 A | 9/1984 | Nusbickel, Jr. et al. | |
| 4,474,064 A | 10/1984 | Naruse et al. | |
| 4,516,583 A * | 5/1985 | Richard | 600/447 |
| 4,559,825 A | 12/1985 | Martens | |
| 4,612,808 A | 9/1986 | McKirdy et al. | |
| 4,730,495 A * | 3/1988 | Green | 73/620 |
| 4,752,895 A | 6/1988 | Sarr | |
| 4,755,953 A | 7/1988 | Geithman et al. | |
| 4,774,842 A | 10/1988 | Kollar et al. | |
| 4,803,638 A | 2/1989 | Nottingham et al. | |
| 4,807,476 A | 2/1989 | Cook et al. | |
| 4,848,159 A | 7/1989 | Kennedy et al. | |
| 4,868,798 A | 9/1989 | Fasnacht, Jr. et al. | |
| 4,912,411 A | 3/1990 | Allison et al. | |
| 5,007,291 A | 4/1991 | Walters et al. | |
| 5,047,771 A | 9/1991 | Engeler et al. | |
| 5,050,703 A | 9/1991 | Graff et al. | |
| 5,062,301 A | 11/1991 | Aleshin et al. | |
| 5,148,414 A | 9/1992 | Graff et al. | |
| 5,164,921 A | 11/1992 | Graff et al. | |
| 5,241,135 A | 8/1993 | Fetzer | |
| 5,396,890 A | 3/1995 | Weng | |
| 5,417,218 A | 5/1995 | Spivey et al. | |
| 5,421,203 A | 6/1995 | Graff et al. | |
| 5,485,084 A | 1/1996 | Duncan et al. | |
| 5,505,089 A | 4/1996 | Weigel | |
| 5,535,628 A | 7/1996 | Rutherford | |
| 5,567,881 A | 10/1996 | Myers | |
| 5,585,564 A | 12/1996 | Brunty et al. | |
| 5,593,633 A | 1/1997 | Dull et al. | |
| 5,621,414 A | 4/1997 | Nakagawa | |
| 5,625,148 A | 4/1997 | Rutherford | |
| 5,677,490 A | 10/1997 | Gunther et al. | |
| 5,698,787 A * | 12/1997 | Parzuchowski et al. | 73/643 |
| 5,786,535 A | 7/1998 | Takeuchi et al. | |
| 5,902,935 A | 5/1999 | Georgeson et al. | |
| 5,963,882 A | 10/1999 | Viertl et al. | |
| 5,986,549 A | 11/1999 | Teodorescu | |
| 6,057,927 A | 5/2000 | Levesque et al. | |
| 6,138,115 A | 10/2000 | Agrawal et al. | |
| 6,167,110 A | 12/2000 | Possin et al. | |
| 6,220,099 B1 | 4/2001 | Marti et al. | |
| 6,474,164 B1 | 11/2002 | Mucciardi et al. | |
| 6,484,583 B1 | 11/2002 | Chennell et al. | |
| 6,507,635 B2 | 1/2003 | Birdwell et al. | |
| 6,516,668 B2 | 2/2003 | Havira et al. | |
| 6,641,535 B2 | 11/2003 | Buschke et al. | |
| 6,658,939 B2 | 12/2003 | Georgeson et al. | |
| 6,711,235 B2 | 3/2004 | Galish et al. | |
| 6,722,202 B1 | 4/2004 | Kennedy et al. | |
| 6,725,721 B2 | 4/2004 | Venczel | |
| 6,748,791 B1 | 6/2004 | Georgeson et al. | |
| 6,772,635 B1 | 8/2004 | Sale et al. | |
| 6,829,959 B2 * | 12/2004 | Gifford et al. | 73/866.5 |
| 6,839,636 B1 | 1/2005 | Sunshine et al. | |
| 6,843,130 B2 | 1/2005 | Georgeson | |
| 6,843,131 B2 | 1/2005 | Graff et al. | |
| 6,843,312 B2 * | 1/2005 | Burk et al. | 165/240 |
| 6,848,312 B2 | 2/2005 | Georgeson | |
| 6,895,079 B2 | 5/2005 | Birdwell et al. | |
| 6,927,560 B2 | 8/2005 | Pedigo et al. | |
| 6,931,931 B2 | 8/2005 | Graff et al. | |
| 7,050,535 B2 | 5/2006 | Georgeson et al. | |
| 7,055,389 B2 | 6/2006 | Mueller | |
| 7,064,332 B2 | 6/2006 | Favro et al. | |
| 7,228,741 B2 | 6/2007 | Georgeson et al. | |
| 7,231,826 B2 | 6/2007 | Bossi et al. | |
| 7,240,556 B2 | 7/2007 | Georgeson et al. | |
| 7,249,512 B2 | 7/2007 | Kennedy et al. | |
| 7,253,908 B2 | 8/2007 | Vaccaro et al. | |
| 7,263,889 B2 | 9/2007 | Kennedy et al. | |
| 7,464,596 B2 * | 12/2008 | Bui et al. | 73/618 |
| 2004/0237653 A1 | 12/2004 | Graff et al. | |
| 2006/0243051 A1 | 11/2006 | Bui et al. | |
| 2007/0006657 A1 | 1/2007 | Kennedy et al. | |
| 2007/0044563 A1 | 3/2007 | Sarr et al. | |

FOREIGN PATENT DOCUMENTS

| | | |
|---|---|---|
| DE | 28 52 560 B1 | 1/1980 |
| DE | 198 26 759 C1 | 12/1999 |
| DE | 100 43 199 A1 | 9/2002 |
| EP | 1 193 491 A2 | 4/2002 |
| JP | 09 264877 A | 10/1997 |

OTHER PUBLICATIONS

U.S. Appl. No. 10/943,135, filed Sep. 16, 2004, Inventors: Georgeson, entitled *Magnetically Attracted Inspecting Apparatus and Method Using a Fluid Bearing*.

U.S. Appl. No. 11/041,499, filed Jan. 24, 2005, Inventors: Kennedy, entitled *Non-Destructive Stringer Inspection Apparatus and Method*.

Stereolithography Made Easy, *What is Rapid Prototyping?*, available at http://www.stereolithography.com/rapidprototyping.php, May 23, 2005, 11 pages.

GE Inspection Technologies: Array Transducers, *Ultrasonic Array Probes*, available at http://www.geinspectiontechnologies.com/products/Ultrasonics/IndustrialProbes/aplparrays.html, dated Mar. 24, 2005, 2 pages.

*Linear Arrays*, available at http://www.ob-ultrasound.net/lineararrays.html, dated Mar. 24, 2005, 2 pages.

* cited by examiner

INTEGRATED CURVED LINEAR ULTRASONIC TRANSDUCER INSPECTION APPARATUS, SYSTEMS, AND METHODS

CROSS-REFERENCE TO RELATED APPLICATIONS

This application is a continuation-in-part of application Ser. No. 11/213,652, entitled "Rapid Prototype Integrated Curved Linear Ultrasonic Transducer Inspection Apparatus, Systems, and Methods," filed Aug. 26, 2005, now U.S. Pat. No. 7,44,876 the contents of which are incorporated herein.

The contents of U.S. Pat. No. 6,722,202; application Ser. No. 10/943,088, entitled "Magnetically Attracted Inspecting Apparatus and Method Using a Ball Bearing," filed Sep. 16, 2004; application Ser. No. 10/943,135, entitled "Magnetically Attracted Inspecting Apparatus and Method Using a Fluid Bearing," filed Sep. 16, 2004; and application Ser. No. 11/041,499, entitled "Non-Destructive Stringer Inspection Apparatus and Method," filed Jan. 24, 2005, are incorporated herein by reference in their entireties.

FIELD OF THE INVENTION

The present invention relates generally to an apparatus and method for inspecting a structure and, more particularly, embodiments of the present invention relate to apparatus, systems, and methods for non-destructive inspection of a structure using curved linear inspection sensors.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing of a structure or after the completed structure has been put into service, including field testing, to validate the integrity and fitness of the structure during manufacturing and ongoing and future use while in-service.

Among the structures that are routinely non-destructively tested are composite structures, such as composite sandwich structures and other adhesively bonded panels and assemblies and structures with contoured surfaces, such as hat stringers or hat stiffeners made from carbon fiber reinforced and graphite epoxy (Gr/Ep) materials and co-cured or co-bonded hat stringers. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo, or impedance sensors may be used to provide indications of voids or porosity, such as in adhesive bondlines of the structure. High resolution inspection of an aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In pulse echo ultrasonic (PEU) testing, ultrasonic sensors, such as ultrasonic transducers, are positioned adjacent to or near one surface of the structure to be inspected. For example, the PEU transducer transmits an ultrasonic signal into the structure under inspection and receives the reflection of the ultrasonic signal from the structure. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. A data acquisition board and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

Non-destructive ultrasonic testing often involves coupling an ultrasonic signal from a transducer or transducer array to the surface of the structure under inspection, such as bubbling water between an inspection device and the structure. While solid laminates may be inspected using one-sided pulse echo ultrasonic (PEU) testing and bondline thickness may be measured using one-sided pulse echo ultrasonic testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display.

Non-destructive inspection may be performed manually by technicians who move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides of a structure which, at least in some circumstances, will be problematic, if not impossible, particularly for semi-automated systems that use a fixed frame for control of automated scan heads.

Automated inspection systems have also been developed as an alternative to manual and semi-automated inspection techniques. For single sided inspection methods, such as pulse echo ultrasonic inspection, a single-arm robotic device, such as an R-2000iA™ series six-axis robot from FANUC Robotics of Rochester Hills, Mich., or an IRB 6600 robot from ABB Ltd. of Zurich, Switzerland, may be used to position and move a pulse echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections.

To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. Similarly, a scanning system may include a linear ultrasonic transducer (also referred to as a linear array transducer, in comparison to an unordered or matrix array). However, typically each structure and inspection application requires a corresponding transducer or transducer array designed to provide transducer alignment (position and orientation with respect to the surface(s) of the structure) and scan coverage for the structure. Conventionally, special inspection devices are constructed for scanning different structures and different sizes and configurations of structures. Designing an inspection device using one or more linear inspection sensors for scanning a particular structure requires ensuring proper alignment of the inspection sensors with respect to the surface(s) of the structure and ensuring scan coverage of the structure. For example, consideration must be taken for flat and curved surfaces as well as features of the structure, including radius features such as convex edges and concave corners. Constructing specialized inspection devices for each inspection application conventionally has required significant time and financial and human resources to design and build these specialized inspection devices. Also, conventionally, each specialized inspection device is designed for and capable of only inspecting one structure, and typically cannot adjust for different sizes of the structure or different inspection applications that use different linear inspection sensor sizes.

Accordingly, a need exists for improved non-destructive inspection apparatus, systems, and methods for inspecting a structure.

SUMMARY OF THE INVENTION

Improved apparatus, systems, and methods are provided for inspecting a structure, such as inspecting structures with one or more curved radius features such as convex edges and concave corners using one or more curved linear inspection sensors, and potentially also inspecting structures having multiple sides using one or more linear inspection sensors. Embodiments of apparatus and systems of the present invention use a sensor holder, typically constructed from rapid prototyping, which is configured to support a curved linear inspection sensor aligned for inspection of a structure with one or more curved radius features, such as hat stringers. Embodiments of methods of the present invention provide fast and efficient methods of constructing custom inspection devices for inspecting structures with curved linear inspection sensors.

According to another aspect of the present invention, to facilitate coupling of ultrasonic signals between curved linear inspection sensors of apparatus and systems of embodiments of the present invention, such as curved linear pulse echo ultrasonic sensors, a couplant may be disposed between the curved linear inspection sensors and a respective surface of the structure under inspection. An apparatus of an embodiment of an inspection device according to the present invention may advantageously include a fluid manifold capable of feeding a fluid couplant between a curved linear inspection sensor and a surface of the structure to couple ultrasonic signals of the curved linear inspection sensor to the structure.

According to another aspect of the present invention, a method for constructing custom inspection devices for inspecting structures with one or more curved linear inspection sensors is provided, such as inspection devices configured to support a curved linear inspection sensor aligned for inspection of a structure.

These and other characteristics, as well as additional details, of the present invention are further described in the Detailed Description with reference to these and other embodiments.

BRIEF DESCRIPTION OF THE DRAWINGS

Figure 1:
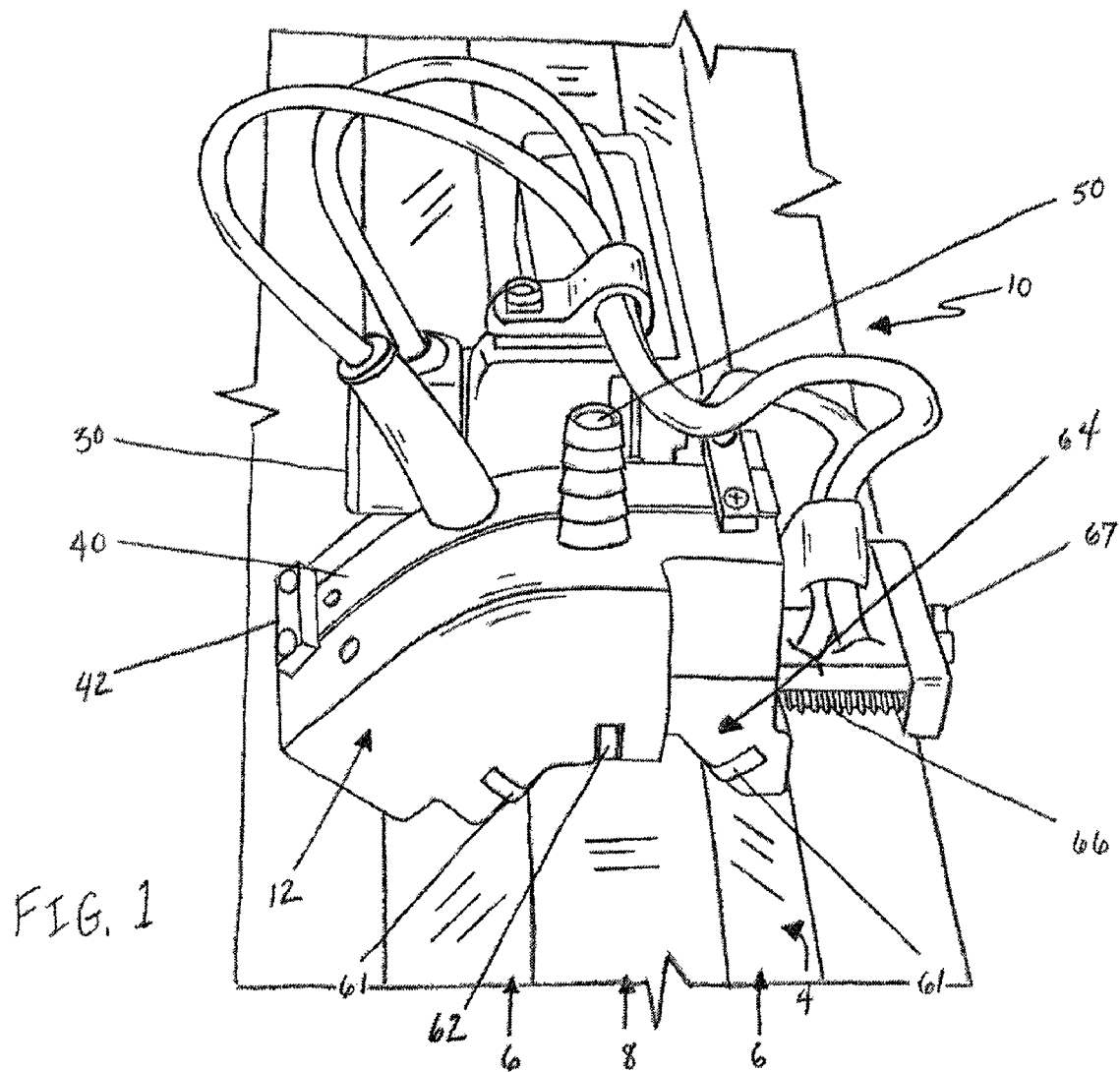
Figure 2:
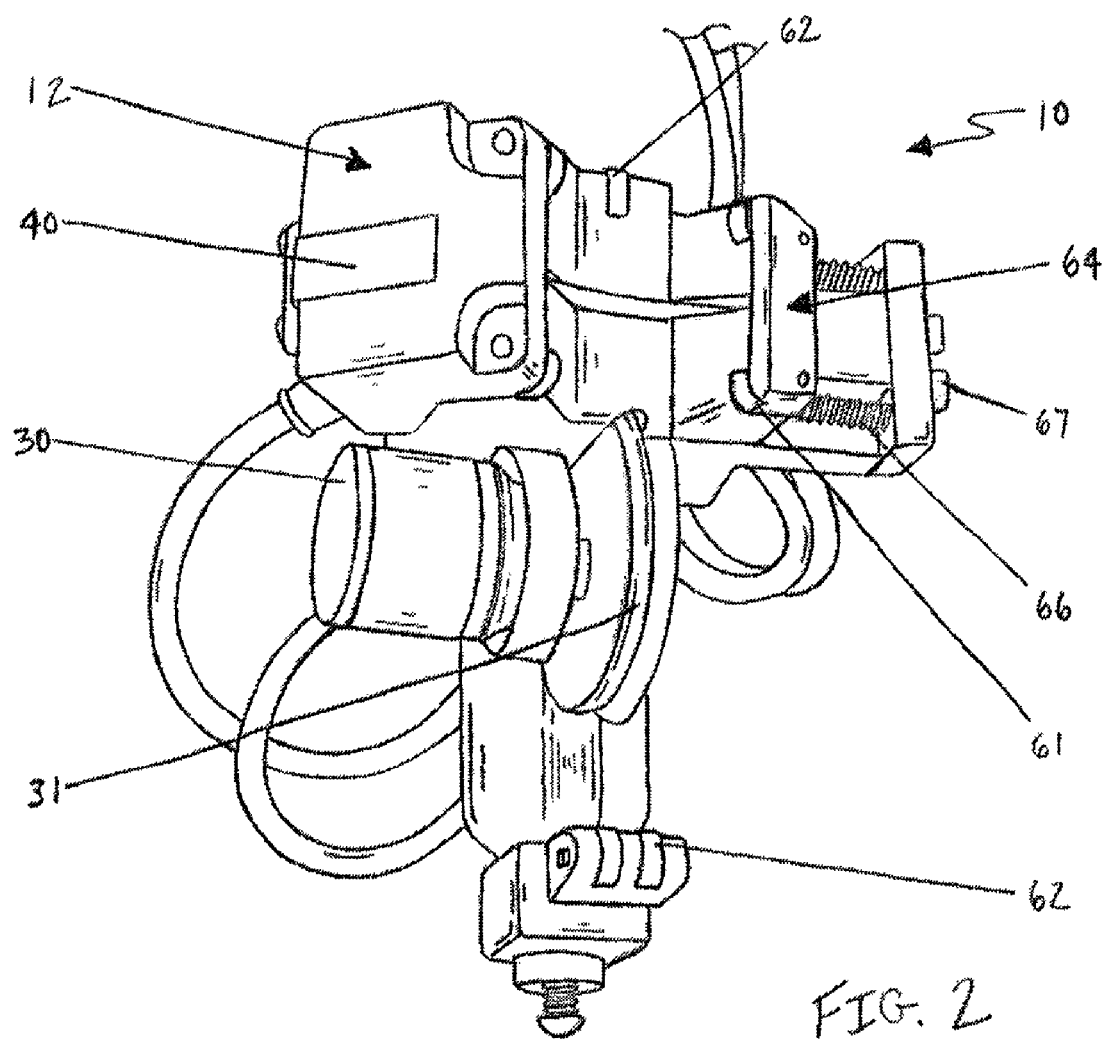

Having thus described the invention in general terms, reference will now be made to the accompanying drawings, which are not necessarily drawn to scale, and wherein:

FIG. 1 is a perspective view of an inspection device of an embodiment of the present invention for inspecting a hat stringer;

FIG. 2 is another view of the inspection device of FIG. 1; and

Figure 3:
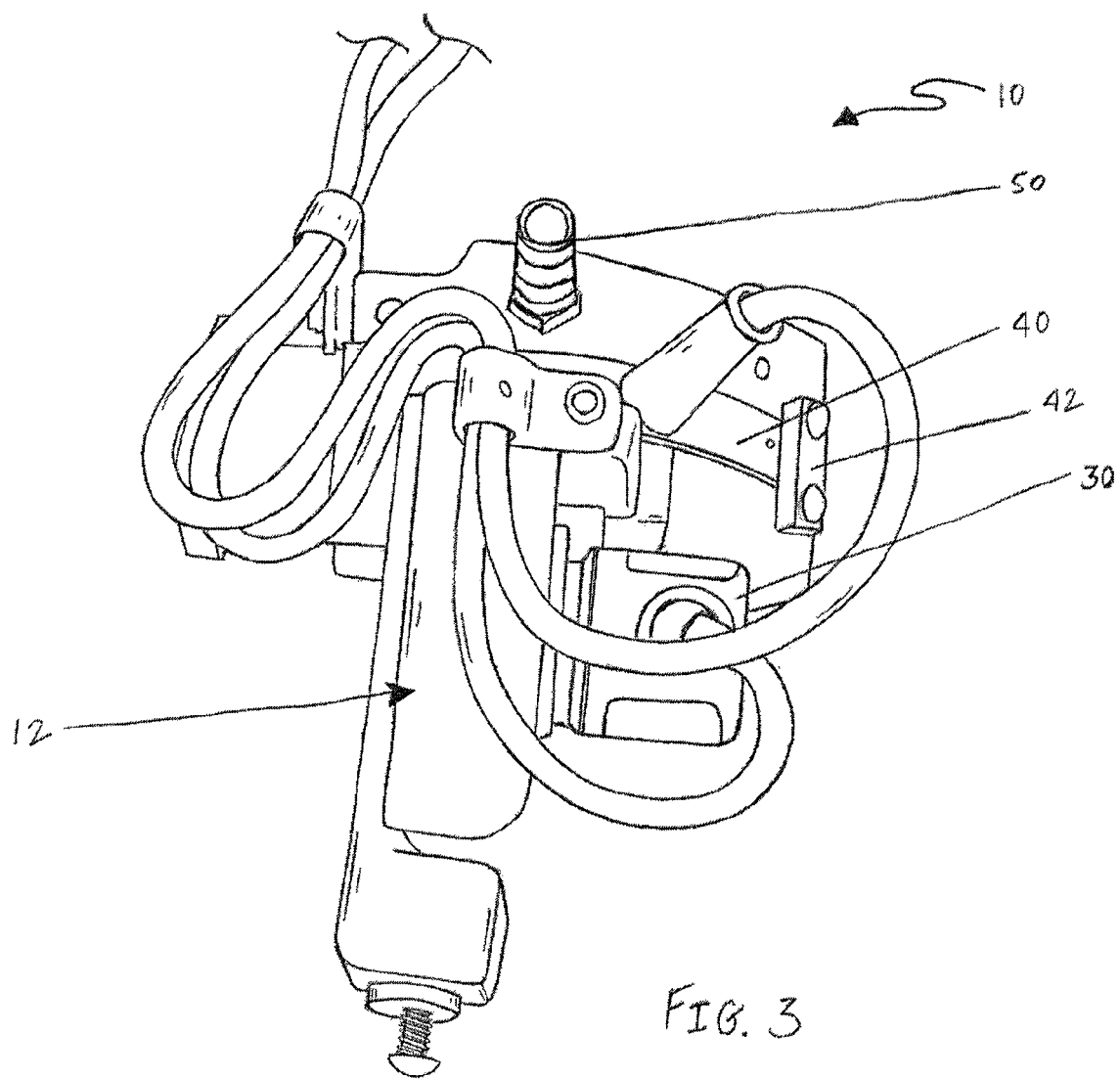

FIG. 3 is yet another view of the inspection device of FIG. 1.

DETAILED DESCRIPTION

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

While embodiments of the present invention are described herein with reference to pulse echo ultrasonic (PEU) non-destructive inspection and typically would be used with curved linear pulse echo ultrasonic non-destructive inspection sensors, embodiments of the present invention are not limited to one-sided inspection methods, but may be used for other inspection methods, including, without limitation, through transmission ultrasonic inspection. For example, inspection of hat stringers and other structures with complex configurations may be more easily inspected using an embodiment of the present invention employing a one sided inspection method such as pulse echo ultrasonic inspection; however, inspection probes, such as magnetically coupled inspection probes, may use embodiments of the present invention for through transmission ultrasonic inspection.

A curved linear inspection sensor, also referred to as a curved linear array, curved linear array inspection sensor, or curved linear transducer, refers to an inspection sensor including a plurality of transducers, typically spaced and arranged at equal distances, which are oriented in either a convex or concave curved shape, such as in a convex shape to inspect a concave curved radius feature or in a concave shape to inspect a convex curved radius feature. The terms curved shape and curved radius feature are used herein to refer to shapes and features which are characteristic of either being smoothly and continuously curved/arcuate or having any other concave or convex shape that is not smoothly and continuously curved, such as a compound curve or linear sections joining at angles. A curved linear array transmits inspection signals at angles through a plane, either diverging if convex or converging if concave. By comparison a linear array transmits inspection signals in parallel through a plane. Using a curved linear inspection sensor is advantageous for inspecting curved radius features of structures, rather than inspecting such curved features using linear inspection sensors transmitting inspection signals in parallel through a plane, even where two linear inspection sensors or two passes of one linear inspection sensor overlap to cover the curved radius feature. A curve linear inspection sensor is better suited to inspect curved radius features than a linear inspection sensor.

Embodiments of integrated linear ultrasonic transducer inspection apparatus, systems, and methods of the present invention are described herein with respect to inspection of hat stringers, especially composite hat stringers for an aircraft fuselage. However, the apparatus, systems, and methods may also be used for structures other than hat stringers and similar applications which require non-destructive inspection, including without limitation other composite structures with difficult-to-inspect geometric configurations and/or remote locations, particularly those with curved radius features. Embodiments of apparatus, systems, and methods of the present invention may be used for manual hand scanning by a technician or using a semi-automatic or automatic motion control system, possibly also using magnetic coupling such as described with reference to the magnetically coupled probes in co-pending application Ser. Nos. 10/943,088; 10/943,135; and 11/041,499. One advantage of rapid prototyping embodiments of the present invention is that rapid prototyping permits creation of inspection devices with custom shapes for custom inspection applications according to the corresponding shapes and features of the structure to be inspected, such as the curved edges and multi-sided surfaces of a hat stringer. Accordingly, embodiments of apparatus and systems according to the invention may be designed and constructed to accommodate variations of structure shapes, sizes, and other characteristics, such as different hat stringer design shapes, sizes, and part thickness changes. A structure of an inspection apparatus for supporting a linear ultrasonic transducer is referred to herein as a sensor holder, whether a rapid prototyping embodiment or fabricated from a conventional method.

An embodiment of an apparatus according to the invention may be designed to have a surface-side (the portion of the apparatus proximate and/or riding on a structure under inspection) of the sensor holder corresponding to the shape of at least a portion of the surface of the structure, where at least a portion of the structure includes a curved feature such as a corner, edge, groove, or non-planar surface such as a convex or concave surface. For example, if the structure to be inspected has a concave shape, the surface-side of the apparatus may be designed to have a convex shape that fits the concave shape of the structure. Similarly, if the structure to be inspected is a hat stringer, the apparatus may be designed to correspond to the shapes, sizes, and corner angles of the hat stringer. For example, an apparatus designed to inspect a convex edge of a hat stringer, may be designed (shaped, sized, etc.) to conform to the structure, to support a curved linear inspection sensor aligned to provide inspection coverage of the convex corner of the hat stringer. For example, the apparatus may include one or more concave corners to respectively match with one or more of the convex corners between the top cap and the web sides of the hat stringer. The portion of a hat stringer including the two convex corners between the top cap and the web sides of the hat stringer may be referred to as the upper radius of the hat stringer. The inspection device of an embodiment of the present invention shown in FIGS. 1-3 include two concave corners to match the two convex corners between the top cap and the web sides of the hat stringer, i.e., to match the upper radius of the hat stringer.

The design and use of a sensor holder according to the present invention permits full coverage inspection of curved radius features of structures using curved linear inspection sensors. A curved linear inspection sensor only inspects in one plane, such as scanning a portion of the y-plane while the x-axis is at a fixed position. However, by using a sensor holder according to the present invention, full inspection coverage is possible. By scanning in a specific pattern, such as placing a curved linear inspection sensor over a curved radius feature, such as across the upper radius of a hat stringer, and then passing the curved linear inspection sensor along the length of the hat stringer, full inspection coverage of the curved radius feature can be achieved.

Inspection devices, and particularly the sensor holders of inspection devices, of embodiments of the present invention are designed to correspond to the shape and size of structures to be inspected. For example, the inspection device 10 depicted in FIGS. 1-3 are intended for inspection of the upper radius portion of hat stringers. For example, the sensor holder 12 of inspection device 10 is designed for traveling over at least a portion of a hat stringer structure for inspecting the top cap and convex corners to the web sides of the hat stringer. The inspection device 10 has concave corners corresponding to the radii of the corners of the web side—top cap intersections of the hat stringer. Similarly, the inspection device 10 is designed with at least a flat top cap surface-side portion designed for traveling over the top cap of a hat stringer. Alternative embodiments may be structured with at least one orientation corner for riding along a corner, in a groove, or with respect to another fixed portion of a structure under inspection, thereby providing orientation between the hat stringer or other structure and the inspection device for a reference and to provide consistency for inspection operations, rather than riding along the upper radius of a hat stringer which implicitly includes two orientation corners on either side of the top cap of the hat stringer, i.e., the curved corners between the top cap and the web sides of the hat stringer.

Embodiments of the present invention may be constructed by rapid prototyping as a single part or in multiple parts which are assembled. For example, a single apparatus may be constructed with (i) rectangular sensor recesses for supporting inspection sensors such as curved linear inspection sensors and/or linear inspection sensors, (ii) a handle for manual inspection operations and handling the inspection device, (iii) a structural holder for supporting an encoder, such as an optical shaft encoder, and (iv) a fluid manifold recess for providing fluid flow from a fluid inlet port to a region between an inspection sensor and a structure, thereby coupling ultrasonic signals of the inspection sensor to the structure. Alternatively, for example, individual pieces of an apparatus may be constructed that can be assembled. Inspection devices, and particularly sensor holders, of embodiments of the present invention may advantageously be fabricated by rapid prototyping (RP, also known as rapid manufacturing, solid freeform fabrication, computer automated manufacturing, and layered manufacturing). Rapid prototyping involves slicing an electronic design model into electronic layers which are physically built up to create the end product, such as stereolithography which constructs three-dimensional end products from liquid photosensitive polymers (e.g., liquid epoxy or acrylate resin) that solidify when exposed to ultraviolet light (e.g., low-power focused UV laser that traces out each layer). Stereolithography is further described in U.S. Pat. No. 4,575,330 to Hull, assigned to 3D Systems, Inc., of Valencia, Calif. Other types of rapid prototyping are also possible, such as laminated object manufacturing, selective laser sintering, fused deposition modeling, solid ground curing, and 3-D ink-jet printing. Rapid prototyping does not require tooling because the end product is produced directly from an electronic design model, typically a CAD model. Because rapid prototyping does not require tooling, it provides a relatively inexpensive and fast method of manufacturing a custom inspection device. Rapid prototyping is particularly advantageous for custom inspection devices because a CAD model can be created for the particular application corresponding to the structure to be inspected, and a corresponding inspection device can be created. Embodiments of the present invention can be created in relatively little time, for relatively low cost while still being designed specifically for a particular inspection application, even if the structure to be inspected has a unique shape or surface contour.

FIGS. 1-3 show an inspection device 10 according to an embodiment of the present invention. FIG. 1 is a top and first end perspective view of the inspection device 10; FIG. 2 is a bottom perspective view of the inspection device 10; and FIG. 3 is a top and second end perspective view of the inspection device 10 opposite that of FIG. 1. FIG. 1 shows the inspection device 10 placed on a hat stringer 4 as the inspection device 10 might be used for an inspection operation of where the inspection device 10 rides along the web sides 6 and top cap 8 of the hat stringer 4.

The inspection device 10 includes a curved linear transducer 40. The curved linear transducer 40 is supported by the rapid prototyped sensor holder 12 of the inspection device 10 in such a manner that the curved linear transducer 40 is oriented to inspect a curved radius feature of the hat stringer, i.e., a curved corner between the web side 6 and top cap 8 of the hat stringer 4. The sensor holder 12 defines a rectangular recesses into which the curved linear transducer 40 is secured, such as by horizontal holders 42 that are screwed down to the sensor holder 12 (or other transducer supports). While the embodiment shown in FIGS. 1-3 defines an enclosed recess, a sensor holder of the present invention may alternatively define a recess or other position into which or against which an inspection sensor is supported and oriented by the sensor holder, and all such structural configurations associated with the support and orientation of an inspection sensor are herein referred to collectively as recesses. Similarly, while a handle for manual operation typically connotes an extension or similar structural member designed specifically and/or solely for gripping and manipulation by an operator, the term handle refers herein to any portion of a sensor holder configured to provide ease of operation of the inspection device by a user, such as the extended portion of the sensor holder surrounding the linear encoder as shown in FIG. 3, or any other part of a sensor holder adapted to be grasped. A sensor holder may be configured to permit adjustment for inspection structures of different shapes and sizes. For example, the sensor holder 12 of FIGS. 1-3 includes an adjustable corner portion 64 which is positioned by adjusting the rotation of alignment screws 66 that control the movement of the adjustable corner portion 64 along the length of the alignment screw 66, thereby adjusting the separation between the web side surface portions of the sensor holder 12 to account for different top cap widths of hat stringers. Similarly, the horizontal holders 42 and rectangular recesses are configured to permit adjustment of the position and size of a curved linear transducer 40 and replacement of the curved linear transducer 40 with curved linear transducers of different lengths or with different curvatures.

An inspection device may also include contact members, such as roller bearings 61, 62 or skids, to extend outwardly from the face or surface of the sensor holder of the inspection device that faces respective surfaces of a structure under inspection. Various types of contact members can be used, such as roller bearings, ball bearings, needle bearings, fluid bearings, skids or the like. Skids may include a Teflon® material available from E.I. DuPont Nemours and Company of Wilmington, Del., on a surface of the skid for contact with the surface of the structure being inspected and to provide for translation thereacross. Skids may be beneficial to prevent damage or marring of a surface of a structure under test when initially placing an inspection device on a structure. Roller, ball, needle, an other types of low-friction bearings may be beneficial for providing ease of motion of the inspection device over the surface of the structure being inspected. Fluid bearings, such as water bearings and air bearings, may be used to maintain spacing and orientation of an inspection device with respect to a structure under inspection. Bearings, skids, and the like may be used to reduce the friction between the inspection device and the surface of the structure under inspection, such as displace the probe from contacting the surface of the structure using hydraulic flotation or a hydrostatic bearing. Use of contact members may provide smooth translation of an inspection device over the surface of a structure to allow an inspection device to maintain an intended direction, maintain alignment of inspection sensors, and allow continuous scanning of a surface regardless of size, smoothness, or flatness of the surface, such as to permit easy rolling of the inspection device. Further, use of a skid or fluid bearing between the inspection device and the surface of the structure may prevent scratching of soft skins or denting of panels of the skins.

For ultrasonic inspection operations, a fluid, like water or air, can be fed through one or more supply lines through a fluid inlet port and into one or more recesses, such as defined channels or manifolds, a central cavity, or similar openings that permit the flow of fluid throughout the inspection device (collectively referred to herein as a "fluid manifold"), within an inspection device to disperse the fluid between the inspection device, and particularly the inspection sensors supported thereby, and the structure, thereby coupling test signals between the inspection sensors and the structure. This process is known as fluid coupling. Generally an attempt is made to have the fluid flow smoothly between the inspection sensors and the structure without bubbles, cavitations, or turbulence that might detrimentally affect the signal to noise ratio of the ultrasonic inspection signals. The inspection device 10 includes a fluid inlet port 50 to which fluid supply lines may be connected to deliver a fluid couplant to the inspection device 10. The fluid inlet port 50 is connected to internal fluid manifolds within the sensor holder 12 that are configured to pass a fluid couplant from the fluid inlet port 50 to the area between the curved linear transducer 40 and the structure under inspection, such as the web side 6 and top cap 8 of the hat stringer 4, and curved corner therebetween. A fluid manifold may be formed of any number of shapes and merely represents a defined passage from a fluid inlet port to an area through which ultrasonic inspection signals pass for controlling the flow of fluid from the fluid inlet prot to the area through which ultrasonic inspection signals pass.

The inspection device 10 also includes an optical shaft encoder (OSE) or linear encoder 30 with a wheel 31 for recording motion or position information of the inspection device 10 with respect to the hat stringer 4 being inspected. The optical shaft encoder 30 and wheel 31 are mounted to the inspection device to operate by traveling along the structure; and alternative embodiments may use encoders which are oriented to operate at different locations than along the top cap position shown in the embodiment of FIGS. 1-3, such as along a web side of a hat stringer or adjacent to the hat stringer, and/or which are mounted in such a manner to permit adjustment as needed for inspection of different structures, such as hat stringers with different heights and/or sizes. Similarly to the use of a wheel attachment 31 for an optical shaft encoder 30, other embodiments of inspection devices in accordance with the present invention may be used with a drive motor or like automated drive mechanism to semi-automatically or automatically move an inspection device along a structure for inspection; alternatively, a magnetically coupled crawler or motion controlled robotic arm maybe use used to control movement of an inspection device along a structure for inspection.

As previously mentioned, embodiments of the present invention may be used in manual scanning operations, such as where an operator slides an inspection device along a structure, or may be used in semi-automated or automated scanning operations. Also, as previously mentioned, sensor holders of embodiments of the present invention may be made in various configurations to conform to equally varying configurations of structures to be scanned using curved linear inspection sensors and/or be adjustable or have exchangeable portions to permit use of a sensor holder on more than one shaped or sized structure. Further, sensor holders and inspection devices of embodiments of the present invention may be used for inspection of multiple portions of a structure, such as with one or more curved linear inspection sensors, and possibly also one or more linear inspection sensors, for scanning curved corners and/or grooves, and possibly web sides and/or a top cap, of a hat stringer, and/or may be used with multiple inspection sensors for simultaneous inspection of different portions of a structure.

The invention should not be limited to the specific disclosed embodiments and modifications and other embodiments of the invention are intended to be included within the scope of the appended claims. Specific terms are used in a generic and descriptive sense only and not for purposes of limitation.

That which is claimed:

1. A non-destructive inspection apparatus for inspecting a structure, comprising:
    a first curved linear inspection sensor; and
    a sensor holder defining a first recess for supporting and orienting the first curved linear inspection sensor, wherein the sensor holder is configured for traveling over at least a first portion of the structure, wherein the first portion of the structure comprises at least a first curved structural feature, and wherein the first recess is configured to orient the first curved linear inspection sensor to inspect the first curved structural feature.

2. The apparatus of claim 1, wherein the sensor holder is configured for inspecting and traveling over at least a portion of a hat stringer, and wherein the first curved structural feature is a curved corner between a web side and a top cap of the hat stringer.

3. The apparatus of claim 2, wherein the sensor holder is configured for spanning the width of the top cap of the hat stringer and both curved corners along the top cap adjacent the web sides of the hat stringer such that the sensor holder straddles the upper radius of the hat stringer.

4. The apparatus of claim 1, wherein the sensor holder further defines a handle for manual inspection of a structure.

5. The apparatus of claim 1, wherein the sensor holder comprises an adjustable portion adapted to relocate to perform at least one of sizing the first recess and defining a position of a concave corner of the sensor holder.

6. The apparatus of claim 5, wherein the adjustable portion comprises an adjustable corner portion adapted to relocate to perform at least defining a position of a concave corner of the sensor holder.

7. The apparatus of claim 5, wherein the sensor holder further comprises an alignment member adapted to control relocation of the adjustable portion.

8. The apparatus of claim 7, wherein the alignment member is an alignment screw adapted to control relocation of the adjustable portion by rotating the alignment screw.

9. The apparatus of claim 1, further comprising at least one removable and adjustable transducer support capable of securing the curved linear inspection sensor in the first recess.

10. The apparatus of claim 1, further comprising a second curved linear inspection sensor, wherein the sensor holder is further configured to define a second recess, wherein the first portion of the structure comprises a second curved structural feature, and wherein the second recess is configured to support and orient the second curved linear inspection sensor to inspect the second curved structural feature while the sensor holder travels over the first portion of the structure.

11. The apparatus of claim 10, wherein the first and second curved structural features are curved corners along a top cap of a hat stringer and the first portion of the structure comprises an upper radius portion of the hat stringer.

12. The apparatus of claim 1, further comprising a second linear inspection sensor, wherein the sensor holder is further configured to define a second recess, wherein the first portion of the structure comprises a first planar structural feature, and wherein the second recess is configured to support and orient the second linear inspection sensor to inspect the first planar structural feature while the sensor holder travels over the first portion of the structure.

13. The apparatus of claim 12, wherein the first planar structural feature is selected from the group of a web side and a top cap of a hat stringer.

14. The apparatus of claim 1, further comprising a fluid manifold and a fluid inlet port connected to the fluid manifold, wherein the fluid inlet port is configured for injecting a fluid into the fluid manifold, and wherein the sensor holder is further configured for permitting the dispersion of fluid from the fluid manifold between the at least one recess and the structure.

15. The apparatus of claim 14, wherein the sensor holder is further configured to define the fluid manifold.

16. The apparatus of claim 14, wherein the fluid manifold is configured for permitting the dispersion of fluid from the fluid manifold between the first curved linear inspection sensor and the structure.

17. The apparatus of claim 1, further comprising an encoder configured for measuring at least one of the following characteristics of the inspection apparatus with respect to the structure under inspection: position, speed, direction, and velocity.

18. The apparatus of claim 1, further comprising a motion device capable of moving the sensor holder over at least the first portion of the structure, wherein the first curved structural feature has a length perpendicular to the curve of the first curved structural feature and a width parallel to the curve of the first curved structural feature, wherein the first curved linear inspection sensor has an end-to-end orientation associated with the width of the first curved structural feature, and wherein the motion device is configured for moving the sensor holder over the structure along an axis perpendicular to the end-to-end orientation of the first curved linear inspection sensor such that the first curved linear inspection sensor moves over the structure for inspection of at least a portion of the length of the first curved structural feature.

19. The apparatus of claim 18, wherein the motion device comprises a motor with an attached wheel.

20. A method of non-destructively inspecting a first curved structural feature of a structure, the method comprising the steps of:
providing a first curved linear inspection sensor adapted for inspection of the first curved structural feature, wherein the first curved structural feature has a length perpendicular to the curve of the first curved structural feature and a width parallel to the curve of the first curved structural feature, and wherein the first curved linear inspection sensor has an end-to-end orientation associated with the width of the first curved structural feature;
supporting and orienting the first curved linear inspection sensor in a first recess defined by a sensor holder, wherein the sensor holder is configured for traveling over at least a first portion of the structure, wherein the first portion of the structure comprises the first curved structural feature, and wherein the first recess is configured to orient the first curved linear inspection sensor to inspect the first curved structural feature; and
translating the first curved linear inspection sensor and sensor holder over the structure along a first axis perpendicular to the end-to-end orientation of the first curved linear inspection sensor such that the first curved linear inspection sensor moves over the structure for inspection of at least a portion of the length of the first curved structural feature.

21. The method of claim 20, wherein the structure is a hat stringer, the first curved structural feature is a radius between a first web side and the top cap of the hat stringer, wherein the hat stringer has a second curved structural feature with a length perpendicular to the curve of the first curved structural feature and a width parallel to the curve of the first curved structural feature, wherein the second curved structural feature is the radius between a second web side and the top cap of the hat stringer, wherein the first curved linear inspection sensor has an end-to-end orientation associated with the width of the second curved structural feature, and the method further comprises the step of translating the first curved linear inspection sensor and sensor holder over the structure along a second axis parallel to the first access and perpendicular to the end-to-end orientation of the second curved linear inspection sensor such that the first curved linear inspection sensor moves over the structure for inspection of at least a portion of the length of the second curved structural feature.

22. The method of claim 20, wherein the sensor holder comprises a fluid manifold and a fluid inlet port connected to the fluid manifold, wherein the fluid inlet port is configured for injecting a fluid into the fluid manifold, and wherein the sensor holder is further configured for permitting the dispersion of fluid from the fluid manifold between the at least one recess and the structure, and the method further comprises the steps of:
injecting a fluid into the fluid manifold; and
dispersing the fluid from the fluid manifold between the at least one recess and the structure.

23. The method of claim 20, wherein the sensor holder comprises an adjustable portion adapted to relocate to perform at least one of sizing the first recess and defining a position of a concave corner of the sensor holder, and the method further comprises the step of relocating the adjustable portion.

24. The method of claim 23, wherein the step of relocating the adjustable portion comprises sizing the first recess.

25. The method of claim 23, wherein the step of relocating the adjustable portion comprises defining a position of a concave corner of the sensor holder.

26. The method of claim 20, further comprising the step of measuring at least one of the following characteristics of the inspection sensor with respect to the structure under inspection: position, speed, direction, and velocity.

* * * * *

UNITED STATES PATENT AND TRADEMARK OFFICE
CERTIFICATE OF CORRECTION

PATENT NO. : 7,617,732 B2
APPLICATION NO. : 11/368557
DATED : November 17, 2009
INVENTOR(S) : Bui et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 654 days.

Signed and Sealed this

Nineteenth Day of October, 2010

David J. Kappos
*Director of the United States Patent and Trademark Office*